US006885451B2

(12) United States Patent
Vogt et al.

(10) Patent No.: US 6,885,451 B2
(45) Date of Patent: Apr. 26, 2005

(54) INFRARED DETECTION OF COMPOSITE ARTICLE COMPONENTS

(75) Inventors: Brian R. Vogt, Oshkosh, WI (US); Charles R. Tomsovic, Omro, WI (US); Jason G. Csida, Reno, TX (US); Mike L. Lohoff, Oshkosh, WI (US); Dale H. Damsteegt, Oshkosh, WI (US); Joseph J. Gimenez, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 191 days.

(21) Appl. No.: 10/210,675

(22) Filed: Jul. 31, 2002

(65) Prior Publication Data

US 2003/0169424 A1 Sep. 11, 2003

Related U.S. Application Data

(60) Provisional application No. 60/362,833, filed on Mar. 9, 2002, provisional application No. 60/372,866, filed on Mar. 9, 2002, provisional application No. 60/364,264, filed on Mar. 14, 2002, provisional application No. 60/364,329, filed on Mar. 14, 2002, and provisional application No. 60/382,812, filed on May 23, 2002.

(51) Int. Cl.[7] .............................................. G01N 21/84
(52) U.S. Cl. ...................................... 356/431; 356/615
(58) Field of Search ................................. 356/614–624, 356/237.1, 429–431; 156/64, 324, 351, 361; 226/28, 29

(56) References Cited

U.S. PATENT DOCUMENTS

| | | |
|---|---|---|
| 2,935,559 A | 5/1960 | Domier |
| 2,984,699 A | 5/1961 | Domier |
| 3,711,176 A | 1/1973 | Alfrey, Jr. et al. |
| 4,166,541 A | 9/1979 | Smith, Jr. |
| 4,170,419 A | 10/1979 | Van Tyne et al. |

(Continued)

FOREIGN PATENT DOCUMENTS

| | | |
|---|---|---|
| EP | 0 043 723 A2 | 1/1982 |
| EP | 0 217 032 B1 | 4/1987 |

(Continued)

OTHER PUBLICATIONS

International Search Report, PCT/US 03/06148, from European Patent Office dated Aug. 8, 2003.
International Search Report, PCT/US 03/06074 dated Aug. 13, 2003, 4 pages.
International Search Report, PCT/US 03/06128 from the European Patent Office dated Aug. 1, 2003.
International Search Report for PCT/US 03/06073 dated Jul. 2, 2003.

*Primary Examiner*—Richard A. Rosenberger
*Assistant Examiner*—Vincent P. Barth
(74) *Attorney, Agent, or Firm*—Senniger Powers

(57) ABSTRACT

A system and process for inspecting an underlying edge of a composite article, such as a disposable absorbent article. The article has first and second panels in at least partially opposed, overlapping engagement with each other. The process and system determine whether the panels of the article are present and/or properly positioned. Also disclosed is a process and system for detecting whether one or more components are present and/or properly positioned in the composite article by use of infrared radiation. Also disclosed is a process and system for defining a window in an image of the article, scanning the defined window to determine a position of the edge and redefining the window in the event that the edge is not located within the defined window during scanning of the defined window.

45 Claims, 9 Drawing Sheets

U.S. PATENT DOCUMENTS

| | | | |
|---|---|---|---|
| 4,543,141 A | 9/1985 | Bradley et al. | |
| 4,614,969 A | 9/1986 | Gerundt et al. | |
| 4,663,220 A | 5/1987 | Wisneski et al. | |
| 4,680,205 A | 7/1987 | Lerner et al. | |
| 4,685,475 A | 8/1987 | Ridler et al. | |
| 4,704,116 A | 11/1987 | Enloe | |
| 4,806,776 A | 2/1989 | Kley | |
| 4,811,002 A | 3/1989 | Otsubo | |
| 4,837,715 A | 6/1989 | Ungpiyakul et al. | |
| 4,877,940 A | 10/1989 | Bangs et al. | |
| 4,900,382 A | 2/1990 | Klose | |
| 4,940,464 A | 7/1990 | Van Gompel et al. | |
| 4,972,093 A | 11/1990 | Cochran et al. | |
| 4,982,103 A | 1/1991 | Meiffren et al. | |
| 5,045,135 A * | 9/1991 | Meissner et al. | 156/64 |
| 5,046,272 A | 9/1991 | Vogt et al. | |
| 5,103,337 A | 4/1992 | Schrenk et al. | |
| 5,104,116 A | 4/1992 | Pohjola | |
| 5,110,403 A | 5/1992 | Ehlert | |
| 5,166,536 A | 11/1992 | Rye | |
| 5,182,722 A | 1/1993 | Hain | |
| 5,204,538 A | 4/1993 | Genovese | |
| 5,224,405 A | 7/1993 | Pohjola | |
| 5,226,992 A | 7/1993 | Morman | |
| 5,235,515 A | 8/1993 | Ungpiyakul et al. | |
| 5,246,433 A | 9/1993 | Hasse et al. | |
| 5,259,526 A | 11/1993 | Pace et al. | |
| 5,286,543 A | 2/1994 | Ungpiyakul et al. | |
| 5,343,049 A | 8/1994 | Vareille et al. | |
| 5,347,135 A | 9/1994 | Harris et al. | |
| 5,359,525 A * | 10/1994 | Weyenberg | 700/124 |
| 5,399,016 A | 3/1995 | Martin | |
| 5,483,893 A | 1/1996 | Isaac et al. | |
| 5,500,063 A | 3/1996 | Jessup | |
| 5,547,531 A | 8/1996 | Allen et al. | |
| 5,549,537 A | 8/1996 | Focke et al. | |
| 5,552,007 A | 9/1996 | Rajala et al. | |
| 5,626,711 A | 5/1997 | Herrmann | |
| 5,635,724 A | 6/1997 | Higgins | |
| 5,637,864 A | 6/1997 | Nicks et al. | |
| 5,644,140 A | 7/1997 | Biedermann et al. | |
| 5,660,666 A | 8/1997 | Dilnik et al. | |
| 5,663,565 A | 9/1997 | Taylor | |
| 5,726,758 A | 3/1998 | Hasegawa et al. | |
| 5,755,902 A | 5/1998 | Reynolds | |
| 5,766,389 A | 6/1998 | Brandon et al. | |
| 5,772,825 A | 6/1998 | Schmitz | |
| 5,779,831 A | 7/1998 | Schmitz | |
| 5,818,719 A | 10/1998 | Brandon et al. | |
| 5,855,574 A | 1/1999 | Kling et al. | |
| 5,858,515 A | 1/1999 | Stokes et al. | |
| 5,870,203 A | 2/1999 | Chiu et al. | |
| 5,879,500 A | 3/1999 | Herrin et al. | |
| 5,930,139 A | 7/1999 | Chapdelaine et al. | |
| 5,980,087 A | 11/1999 | Brandon et al. | |
| 6,040,903 A | 3/2000 | Lysen et al. | |
| 6,067,155 A | 5/2000 | Ringlien | |
| 6,082,732 A | 7/2000 | Hutchison et al. | |
| 6,092,002 A | 7/2000 | Kastman et al. | |
| 6,166,393 A | 12/2000 | Paul et al. | |
| 6,198,102 B1 | 3/2001 | Shepherd | |
| 6,217,794 B1 | 4/2001 | Neal et al. | |
| 6,224,699 B1 | 5/2001 | Bett et al. | |
| 6,245,168 B1 | 6/2001 | Coenen et al. | |
| 6,253,159 B1 | 6/2001 | Bett et al. | |
| 6,270,599 B1 | 8/2001 | Wood | |
| 6,323,954 B1 | 11/2001 | Halter | |
| 6,352,497 B1 | 3/2002 | Hensley et al. | |
| 6,444,064 B1 * | 9/2002 | Henry et al. | 156/64 |
| 2001/0016059 A1 | 8/2001 | Krahn et al. | |
| 2002/0000291 A1 | 1/2002 | Coenen et al. | |
| 2002/0055430 A1 | 5/2002 | Coenen et al. | |

FOREIGN PATENT DOCUMENTS

| | | |
|---|---|---|
| EP | 0 217 032 A3 | 8/1987 |
| EP | 0 217 032 B1 | 8/1987 |
| EP | 0 320 991 A2 | 6/1989 |
| EP | 0 328 890 A1 | 8/1989 |
| EP | 0 554 911 A1 | 8/1993 |
| WO | WO 96/17303 A1 | 6/1996 |
| WO | WO 96/19346 A2 | 6/1996 |
| WO | WO 96/19347 A2 | 6/1996 |
| WO | WO 99/36809 A1 | 7/1999 |
| WO | WO 99/36810 A1 | 7/1999 |
| WO | WO 00/37009 A2 | 6/2000 |
| WO | WO 00/40196 A1 | 7/2000 |
| WO | WO 00/45767 A1 | 8/2000 |
| WO | WO 01/83347 A1 | 11/2001 |
| WO | WO 01/87210 A1 | 11/2001 |
| WO | WO 01/87211 A2 | 11/2001 |
| WO | WO 01/87211 A3 | 11/2001 |
| WO | WO 01/87218 A2 | 11/2001 |
| WO | WO 01/87562 A2 | 11/2001 |
| WO | WO 01/87753 A3 | 11/2001 |
| WO | WO 01/87753 A2 | 11/2001 |

* cited by examiner

INFRARED DETECTION OF COMPOSITE ARTICLE COMPONENTS

BACKGROUND OF THE INVENTION

The present invention relates to detecting the presence and/or position of one or more components, such as edges, in a composite article, and to registration inspection of composite articles using radiation and detectors.

A vast number of applications exist in which it is necessary or desirable to monitor the presence and/or position of one or more components of a composite article during manufacturing. For instance, in a largely automated process for manufacturing disposable absorbent products such as diapers and other incontinence products, certain components (e.g., support layers, absorbent pads, elastic components, fastener components, etc.) must be positioned or aligned with respect to each other and/or other components in order to produce an acceptable product. Accordingly, inspection systems are commonly used to detect the positions of such components during manufacturing. If an inspection system determines that one or more components are out of position and thus do not properly register with other components, the inspection system typically outputs one or more signals indicating that certain articles should be culled and discarded, that the process should be adjusted so as to bring out-of-position components into proper position, that the process should be adjusted so that subsequent components are brought into proper registration with one another, etc.

An exemplary registration inspection system is disclosed in U.S. Pat. No. 5,359,525, the disclosure of which is incorporated herein by reference. As described therein, registration inspection of a composite article undergoing fabrication is accomplished by producing an image of the article and then analyzing the image to detect the position of one or more components. The detected positions are then compared to ideal positions to thereby determine whether the one or more components are properly positioned. This registration inspection system employs conventional video cameras for capturing visible and ultraviolet light reflected by and/or transmitted through components in order to produce still video images of such components. Thus, after producing a video image of a composite article and its several components, the image can be analyzed to determine whether the components are properly positioned and registered with one another.

Although highly useful for many applications, the inventors hereof have determined that the inspection system disclosed in the aforementioned patent, and similar systems, have certain shortcomings. For example, such systems are not well suited for determining the presence and/or positions of components underlying other components or components which are substantially opaque to visible and/or ultraviolet light. Additionally, such systems are not well suited to determining the presence and/or positions of components which tend to scatter visible and ultraviolet light.

Another exemplary inspection system, disclosed in U.S. Pat. No. 6,224,699, employs infrared detectors for producing infrared images of products undergoing formation by sensing infrared radiation emitted by heated product components. The produced images are then compared with reference information to determine, for example, whether the product components are properly positioned. However, this system is not well suited to detecting product components which have cooled, or which were never heated in the first instance.

The inventors hereof have also recognized that prior art inspection systems and processes are not well suited to detecting the position of certain product components.

SUMMARY OF THE INVENTION

In order to solve these and other needs in the art, the inventors hereof have succeeded at designing processes and systems for detecting the position of one or more components in a composite article, including adjacent components, overlapping components, and components which overlie or underlie other components, including components which are disposed or sandwiched between other components. The present invention also relates to composite articles produced or inspected using such processes and systems. The invention is especially well suited to detecting properties of disposable absorbent articles undergoing fabrication and/or quality inspection, although the invention is far from so limited, as will be apparent from the description below.

In one form, the invention includes a process of inspecting a composite article having first and second panels in at least partially opposed, overlapping engagement with each other and having an underlying edge. The process determines whether the panels of the article are present and/or properly positioned. The overlapping engagement of the panels is irradiated with radiation. An image is produced from radiation received from the irradiated panels. A position of the underlying edge is identified in the image. The identified position of the underlying edge is compared with a predetermined data to thereby determine whether the underlying edge is present and/or properly positioned in the composite article.

In another form, the invention includes a system for inspecting a composite article having first and second panels in at least partially opposed, overlapping engagement with each other and having an underlying edge. The system determines whether the panels of the article are present and/or properly positioned. A radiation source irradiates the overlapping engagement of the panels with radiation. A detector produces an image from radiation received from the irradiated panels. An image analyzer operatively connected to the detector identifies in the image a presence and/or position of the underlying edge and compares the identified presence and/or position of the underlying edge with a predetermined data to thereby determine whether the underlying edge is present and/or properly positioned in the composite article.

In another form, the invention includes a process of detecting one or more components in a composite article. The composite article is irradiated with infrared radiation. An image is produced from infrared radiation received from the irradiated composite article. A position in the produced image corresponding to an edge position of a first component in the composite article is identified. The identified position is compared with predetermined position data to thereby determine whether the first component is present and/or properly positioned in the composite article.

In another form, the invention includes a system for detecting one or more components in a composite article. An infrared radiation source irradiates the composite article with infrared radiation. An infrared detector produces an image from infrared radiation received from the irradiated composite article. An image analyzer operatively connected to the infrared detector identifies a position in the produced image corresponding to an edge position of a first component in the composite article and compares the identified position with predetermined position data to thereby determine whether the first component is present and/or properly positioned in the composite article.

In another form, the invention includes a process of inspecting a composite article having first and second panels in at least partially opposed, overlapping engagement with each other and having an edge. The process determines whether the panels of the article are properly positioned. The process comprises:

irradiating the overlapping engagement of the panels with radiation;

producing an image from radiation received from the irradiated panels;

defining a window in the image;

scanning the defined window to determine a position of the edge;

redefining the window in the event that the edge is not located within the defined window during the scanning of the defined window; and comparing the determined position of the edge with a predetermined data to thereby determine whether the edge is properly positioned in the composite article.

In another form, the invention includes a system for inspecting a composite article having first and second panels in at least partially opposed, overlapping engagement with each other and having an edge. The system determines whether the panels of the article are properly positioned. A radiation source irradiates the overlapping engagement of the panels with radiation. A detector produces an image from radiation received from the irradiated panels. An image analyzer operatively connected to the detector defines a window in the image, scans the defined window to determine a position of the edge, redefines the window in the event that the edge is not located within the defined window during the scanning of the defined window, and compares the determined position of the edge with a predetermined data to thereby determine whether the edge is properly positioned in the composite article.

BRIEF DESCRIPTION OF THE DRAWINGS

FIG. 12 corresponds to FIG. 11 with a rotated tool to detect an edge of the overlying panel.

Corresponding reference characters indicate corresponding features throughout the several views of the drawings.

DETAILED DESCRIPTION OF THE DRAWINGS

The methods and apparatus of the present invention can be used to make a variety of pre-fastened articles such as disposable absorbent garments including diapers, training pants, feminine hygiene products, incontinence products, medical garments, other personal care or health care garments, swim pants, athletic clothing, pants and shorts, and the like. More particularly, the methods and apparatus of the present invention can be used to make articles in which at least two elements of the article are connected together during the making thereof to assemble or "pre-fasten" the article. For ease of explanation, the methods and apparatus of the present invention are hereafter described in connection with making pre-fastened child's training pants, generally indicated as 20 in FIG. 1. In particular, the methods and apparatus will be described in terms of those for making pre-fastened disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Training pants 20 can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

Figure 1:
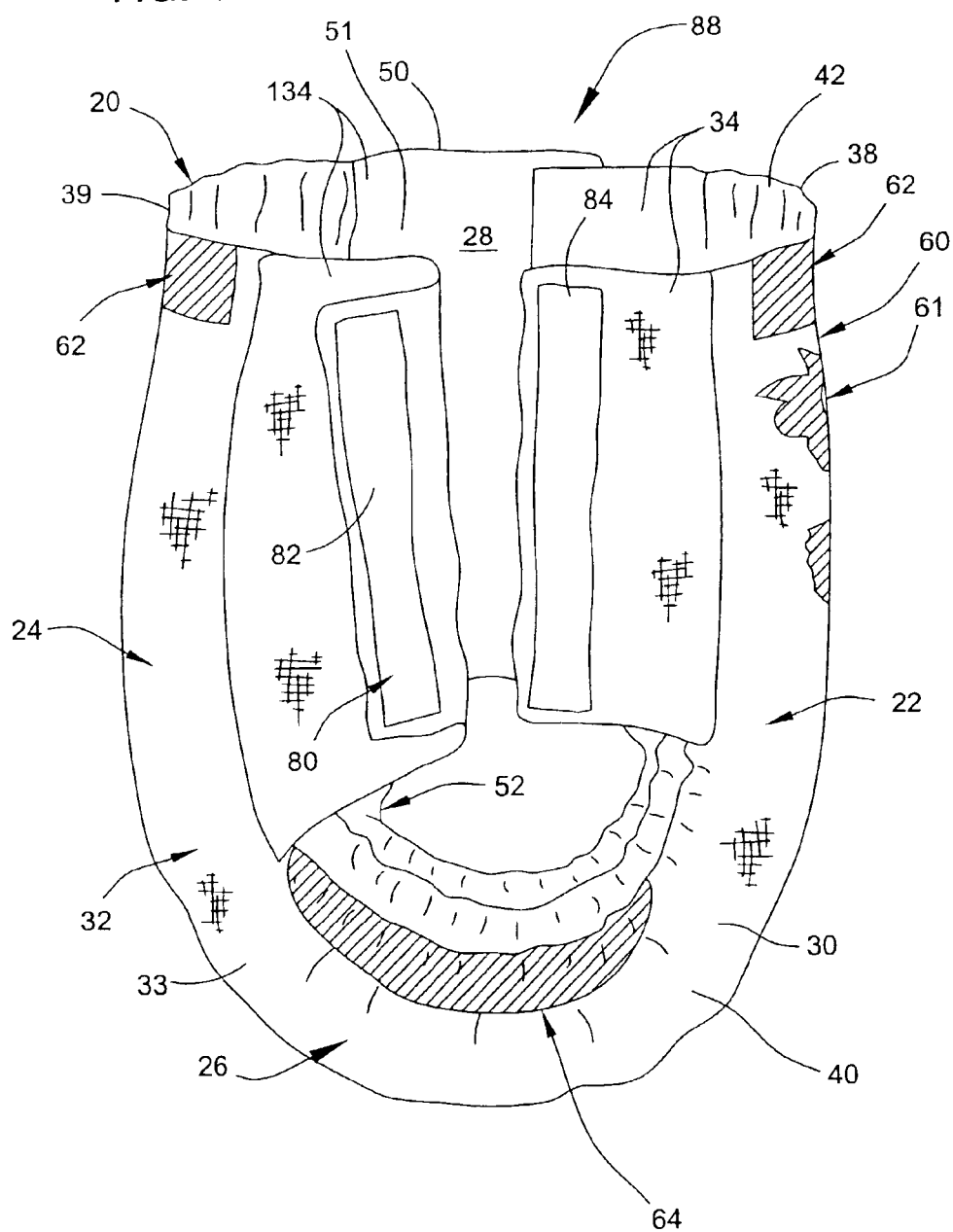
FIG. 1 is a side elevation of a child's training pants with a fastening system of the training pants shown connected on one side of the training pants and disconnected on the other side of the training pants.

With reference now to the drawings, and in particular to FIG. 1, a pair of training pants 20 is illustrated in a partially fastened condition and comprise an absorbent chassis 32 having a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
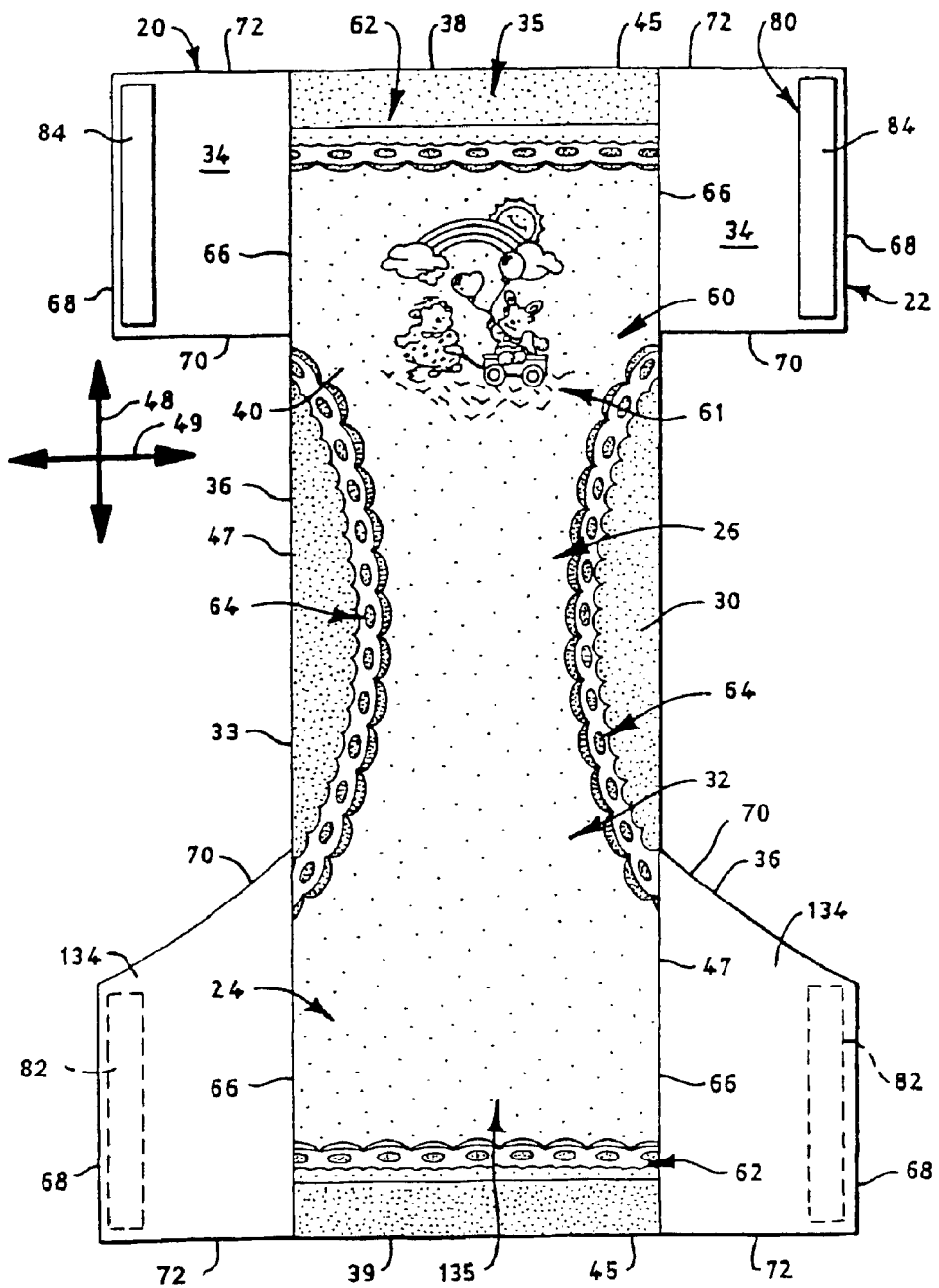
FIG. 2 is a bottom plan view of the training pants of FIG. 1 in an unfastened, stretched and laid flat condition to show the surface of the training pants which faces away from the wearer.
Figure 3:
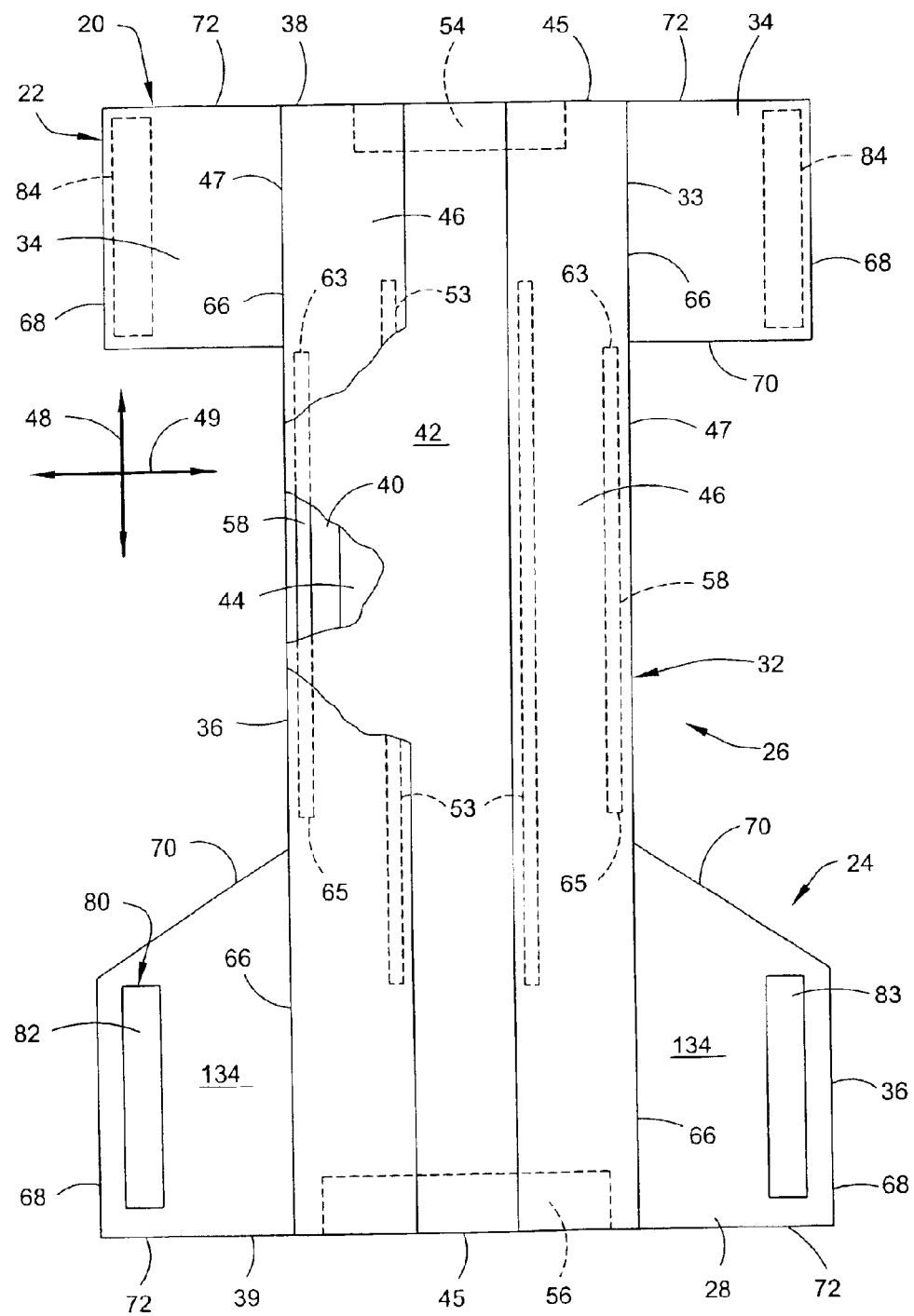
FIG. 3 is a top plan view of the training pants in its unfastened, stretched and laid flat condition to show the surface of the training pants which faces the wearer when the training pants are worn, with portions of the training pants being cut away to reveal underlying features.

The illustrated absorbent chassis 32 comprises a composite structure 33 (FIG. 3), which when laid flat can be rectangular or any other desired shape, and has a pair of laterally opposite front side panels 34 and a pair of laterally opposite back side panels 134 extending outward therefrom. The composite structure 33 and side panels 34, 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and could define a one-piece elastic, stretchable, or nonstretchable pants. The illustrated composite structure 33 comprises an outer cover 40, a bodyside liner 42 (FIGS. 1 and 3) connected to the outer cover in a superposed relation, an absorbent assembly 44 (FIG. 3) disposed between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having an interior space 51, a waist opening 50 for receiving the wearer into the interior space of the pants, a pair of leg openings 52 and engagement seams 88 along which the side panels are connected. The interior space 51 of the pants 20 is thus bounded by the absorbent chassis 32, the engagement seams 88 and the portions of the side panels 34, 134 extending on opposite sides of the engagement seams 88 (e.g., between the engagement seams and the absorbent chassis. As used herein, the "interior space" 51 is intended to refer to the space between any two portions of a three-dimensional article which generally oppose each other. It is understood that a transverse cross-section of the article need not be closed, e.g., continuous, to define the interior space 51. For example, a two-dimensional article may be generally folded over on itself so that two portions of the article oppose each other to define an interior space of the article therebetween. Thus, the interior space 51 of the training pants 20 shown in FIG. 1 may be defined by the side panels 34, 134 themselves or, if the side panels are fully straightened therebetween, the interior space is defined by a combination of the side panels and the front and back waist regions 22, 24 of the absorbent chassis 32.

The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA$^7$ and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing,as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumberg, Ill., U.S.A.

If the outer cover 40 is a single layer of material, it can be embossed and/or matte finished to provide a more cloth-like appearance. As earlier mentioned, the liquid impermeable material can permit vapors to escape from the interior space 51 of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of training pants 20 is designed for use by young girls and includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling,and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants 20 can comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in training pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the attachment line 66 to the outer edge 68, as is best shown in FIGS. 2 and 3.

Each of the side panels 34, 134 can include one or more individual, distinct pieces of material. In particular embodiments, for example, each side panel 34, 134 can include first and second side panel portions that are joined at a seam, or can include a single piece of material which is folded over upon itself (not shown).

The side panels 34, 134 desirably although not necessarily comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No.

5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes first fastening components 82 adapted for refastenable engagement to corresponding second fastening components 84. In one embodiment, one surface of each of the first fastening components 82, 84 comprises a plurality of engaging elements which project from that surface. The engaging elements of the first fastening components 82 are adapted to repeatedly engage and disengage engaging elements of the second fastening components 84.

The fastening components 82, 84 can comprise separate elements bonded to the side panels 134, 34, or they may be integrally formed with the side panels. Thus, unless otherwise specified, the term Afastening component@ includes separate components which function as fasteners, and regions of materials such as the side panels 34, 134 which function as fasteners. Moreover, a single material can define multiple fastening components to the extent that different regions of the material function as separate fasteners. The fastening components 82, 84 can be located on the side panels 134, 34, between the side panels such as on the absorbent chassis, or a combination of the two.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

The refastenable fastening system 80 allows for easy inspection of the interior space 51 of the pants 20. When necessary, the fastening system 80 also allows the pants 20 to be removed quickly and easily. This is particularly beneficial when the pants contain messy excrement. For training pants 20, the caregiver can completely remove the pants 20 and replace it with a new one without having to remove the child=s shoes and clothing.

In the illustrated embodiment, the first fastening components 82 comprise loop fasteners and the second fastening components 84 comprise complementary hook fasteners. Alternatively, the first fastening components 82 comprise hook fasteners and the second fastening components 84 comprise complementary loop fasteners, or the fastening components 82, 84 can comprise interlocking similar surface fasteners, adhesive or cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height, a greater percentage of directionally-aligned hooks, or a more aggressive hook shape.

Loop fasteners typically comprise a fabric or material having a base or backing structure and a plurality of loop members extending up from at least one surface of the backing structure. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook fasteners typically comprise a fabric or material having a base or backing structure and a plurality of hook members extending upwardly from at least one surface of the backing structure. In contrast to the loop fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded from nylon, polypropylene or another suitable material. Suitable single-sided hook materials for the fastening components are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 3, the fastening components 82 are disposed on the inner surface 28 of the back side panels 134. The fastening components 82 are desirably positioned along the outer edges 68 of the back side panels 134, and abutting or adjacent to the waist end edge 72. In certain embodiments, for example, the fastening components 82 can be spaced inward from the outer edges 68 of the front side panels 34 in the range of about 0 to 25 mm. With particular reference to FIG. 2, the second fastening components 84 are disposed on the outer surface 30 of the front side panels 134. The second fastening components 84 are sized to receive the first fastening components 82 and are desirably positioned along the outer edges 68 of the front side panels 34, and abutting or adjacent to the waist end edge 72. As an example, the second fastening components 84 can be spaced inward from the outer edges 68 of the back side panels 134 in the range of about 0 to 25 mm. It is understood that the fastening components 82, 84 may also extend laterally out beyond the outer edges 68 of the side panels 34, 134. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 84, 82 can be adhered to the respective side panels 34, 134 by any means known to those skilled in the art such as adhesive bonds, ultrasonic bonds or thermal bonds. The fastening components 82, 84 may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components 82, 84 can comprise integral portions of the waist regions 24, 22. For instance, one of the elastomeric front or back side panels 34, 134 can function as second fastening components 84 in that they can comprise a material which is releasably engageable with fastening components 82 disposed in the opposite waist region.

The fastening components 82, 84 of the illustrated embodiments are rectangular, although they may alternatively be square, round, oval, curved or otherwise non-rectangularly shaped. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 50 to about 130 mm, such as about 100 mm, and the width is desirably from about 50 to about 30 mm, such as about 10 mm. With particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

As shown in FIG. 1, when the fastening components 82, 84 are releasably connected, the side edges 36 of the absorbent chassis 32 in the crotch region 26 define the leg openings 52, and the waist edges 38 and 39 of the absorbent chassis, including the waist end edges 72 of the side panels 34, 134, define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When connected, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 80 to 100 percent, and particularly about 90 to about 98 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 80 to 100 percent, and more particularly about 90 to about 98 percent, of the distance between the waist end edge 70 and the leg end edge 72 of the side panels 34, 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

For the engagement seams 88 to be located, at the sides of the wearer, it can be particularly desirable for the transverse distance between the fastening components 82 of the back side panels 134 to be substantially equal to the transverse distance between the fastening components 84 of the front side panel 134. The transverse distance between each respective set of fastening components 82, 84 is measured parallel to the transverse axis 49 between the longitudinal center lines of the respective fastening components, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may be only partially laterally opposite each other, such as by being offset longitudinally, without departing from the scope of this invention.

Figure 4:
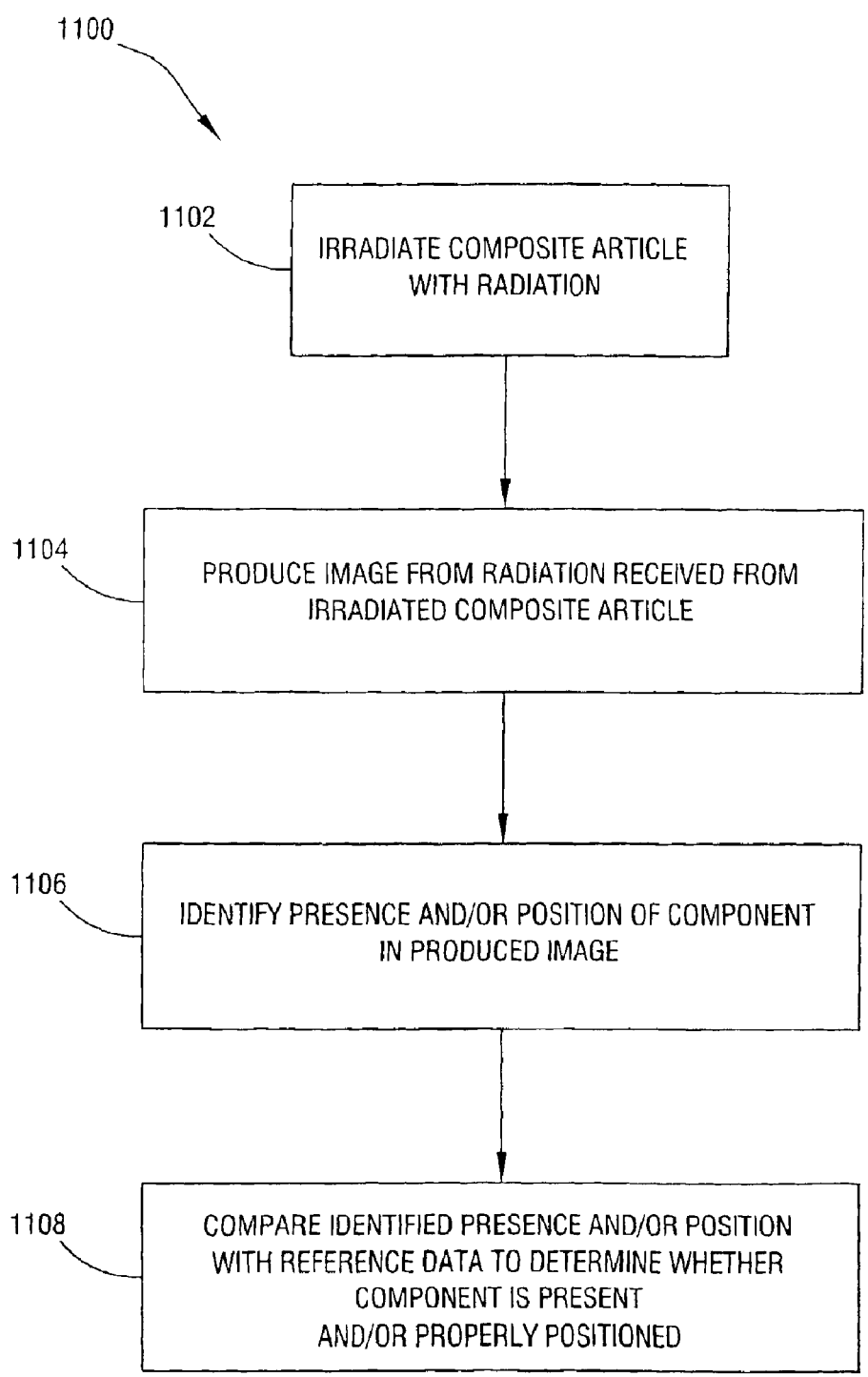
FIG. 4 is a flow diagram of a process for detecting whether one or more components are properly positioned in a composite article according to one preferred embodiment of the present invention.

FIG. 4 illustrates a process as indicated generally by reference character 1100 of inspecting a composite article, such as an article having first and second panels in at least partially opposed, overlapping engagement with each other to determine whether the panels of the article are present and/or properly positioned. The process 1100 includes irradiating the composite article with radiation as shown in block 1102 of FIG. 4, and producing an image from radiation received from the irradiated composite article, as shown in block 1104. For example, when inspecting the composite article 1500 having panels 1502, 1504 and fastener 1506 shown in FIG. 8, the overlapping engagement of the panels would be irradiated and the image from radiation received from the radiated panels and a fastener 1506 therebetween would be produced. The process further includes, in block 1106, identifying the presence and/or position of one or more components in the produced image of the composite article. In one embodiment of the invention, an underlying edge as described herein would be identified. In block 1108, the identified presence and/or position of the component(s) in the produced image (in block 1106) is compared with reference data to thereby determine whether the component(s) of the composite article is present and/or properly positioned therein.

In one embodiment of the invention, infrared radiation would be used to irradiate the overlapping engagement. By utilizing infrared radiation rather than (or in addition to)

visible light, the process 1100 can not only detect the presence and/or position of components which tend to scatter visible and ultraviolet light, including components which overlie other components, but also the presence and/or position of components which underlie other components, including components disposed or sandwiched between components which are substantially opaque to visible and ultraviolet light, as further explained herein.

Figure 5:
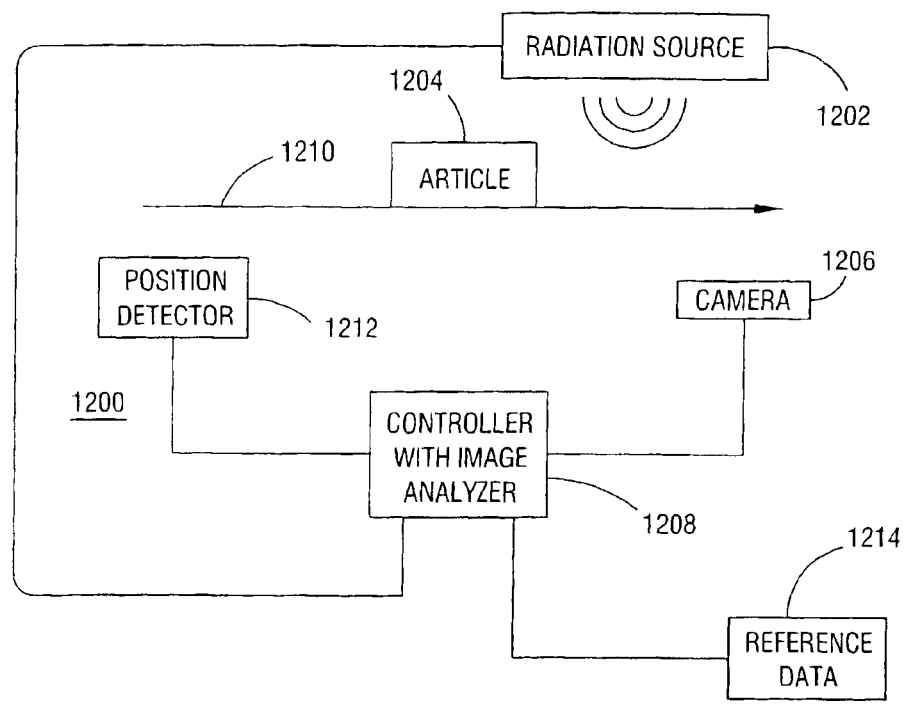
FIG. 5 is a block diagram of an exemplary system for implementing various aspects of the present invention, including the process of FIG. 4, where a composite article is positioned between a camera or other detector and a light source or other radiation source.

One exemplary system 1200 for implementing the process 1100 of FIG. 4 (and other aspects of the present invention) is illustrated in FIG. 5. For example, system 1200 may be used to inspect composite articles having first and second panels in at least partially opposed, overlapping engagement with each other and having an underlying edge for determining whether the panels of the article are present and properly positioned. As shown in FIG. 5, the system 1200 includes a radiation source 1202, such as an infrared source, for irradiating a composite article 1204 with infrared radiation. For example, source 1202 may irradiate the overlapping engagement of the panels of the article noted above. The system 1200 further includes an infrared image capturing device such as a camera 1206 for producing, in this example, a two dimensional image from radiation transmitted through the composite article 1204 and received from the irradiated panels. The camera 1206 is operatively connected to a controller with image analyzer 1208, which itself is operatively connected to the camera 1206 for identifying in the image a presence and/or position of a component, such as a position of an edge, and for comparing the identified presence and/or position with predetermined (reference) data 1214 to thereby determine whether the edge is properly positioned in the composite article.

The arrow 1210 in FIG. 5 is intended to represent optional constant or intermittent (e.g., periodic) movement of the composite article 1204 relative to the system 1200. In one embodiment, the composite article 1204 is moved into a field of view of the camera 1206 for inspection as detected by a position detector 1212 which alerts the controller with image analyzer 1208 that an article is in the camera's field of view. Alternatively (or additionally), the camera 1206 may be moved (or have components which are moved, such as in a scanning motion) for inspection of the composite article. Alternatively, the camera 1206 may be a line scanner which scans a line of the article 1204 as it moves past the scanner and recreates the image of the article after the entire article is scanned.

The radiation source 1202 may emit infrared radiation (i.e., radiation having a wavelength between about 700 nanometers and 1 millimeter) continuously or intermittently. If the radiation source 1202 emits continuously, the camera 1206 may be an infrared detector shuttered (electronically or otherwise) to prevent blurring of the image due to high speed movement of the composite article, if applicable. If the radiation source emits radiation intermittently, the camera 1206 and image capturing by the controller and image analyzer 1208 may be synchronized with the radiation source 1202 by a position detector 1212 so as to produce an image contemporaneously with the irradiating of the composite article.

The controller with image analyzer 1208 is configured to receive the image produced by the camera 1206. This image will include variations therein which correspond to variations in radiation levels (and/or wavelengths) received by the camera 1206 from a top side of the composite article 1204. In one embodiment, the image produced by the camera is a black-and-white image in which radiation level variations are depicted in varying grayscale levels. Alternatively, such variations may be depicted in the image in another manner, such as in the form of color variations. Regardless of their form, the image analyzer 1208 may be configured to identify the presence and/or position of one or more variations in the produced image each corresponding to a component in the composite article. These identifications are then compared by a compare routine or other software which is part of controller 1208 with reference data 1214 (e.g., ideal, previous or predetermined position data) to determine whether the positions of components in the composite article are acceptable. For example, the comparison may determine whether the edge position of a particular component is precisely where it is supposed to be, or whether it falls within a predetermined range of acceptable positions.

The image analyzer 1208 can be configured to determine the positions of variations in the image produced by the camera 1206, and thus the edge positions of components in the composite article 1204, either as fixed positions or relative positions, or a combination of both. Thus, the image analyzer may determine the edge position of a composite article component relative to a fixed point, edge or region of or in the image, relative to another component or the edge of another component in the image, relative to a registration mark on or about a component of the composite article, etc. As one example, the image analyzer may first determine the edge position of a first component as a fixed position (e.g., in terms of x,y coordinates or, in the case of a three dimensional image, in terms of x,y,z coordinates), and then determine the edge position of a second component (or another edge position of the first component) relative to the previously determined edge position of the first component.

The analyzer 1208 may be configured to compare identified positions with reference data (e.g., predetermined fixed and/or relative position data, as applicable) to thereby determine whether one or more components are properly present and positioned in the composite article. Depending on the outcome of such comparison(s), the analyzer may output one or more signals to a process controller (not shown) indicating that one or more composite articles should be culled and discarded, that the process should be adjusted so as to bring out-of-position components into proper position, that the process should be adjusted so that subsequent components are brought into proper registration with one another, etc. An operator alarm (such as an audible alarm or a visible alarm, such as one provided on a closed circuit monitor or television; not shown) may also be provided upon determining that one or more components of a composite article, or a series of composite articles, are mispositioned, and may display an image of the composite article or the components thereof to an operator for monitoring, tracking or diagnostic purposes.

As an example, the following off-the-shelf commercial products may be employed to constitute the system 1200 according to the invention. The radiation source 1202 may be from Fostic Strobe Lighting such a universal ring lights made by Schott-Fostec, LLC or the LED array 3–5 MM noted above. The camera 1206 may be a Sony XC-73 series or XC-75 series mounted on a Optosigma Optical Carrier, as noted above. The controller with image analyzer 1208 may be PC interfacing with a Cognex 800 Vision Processor.

Figure 6:
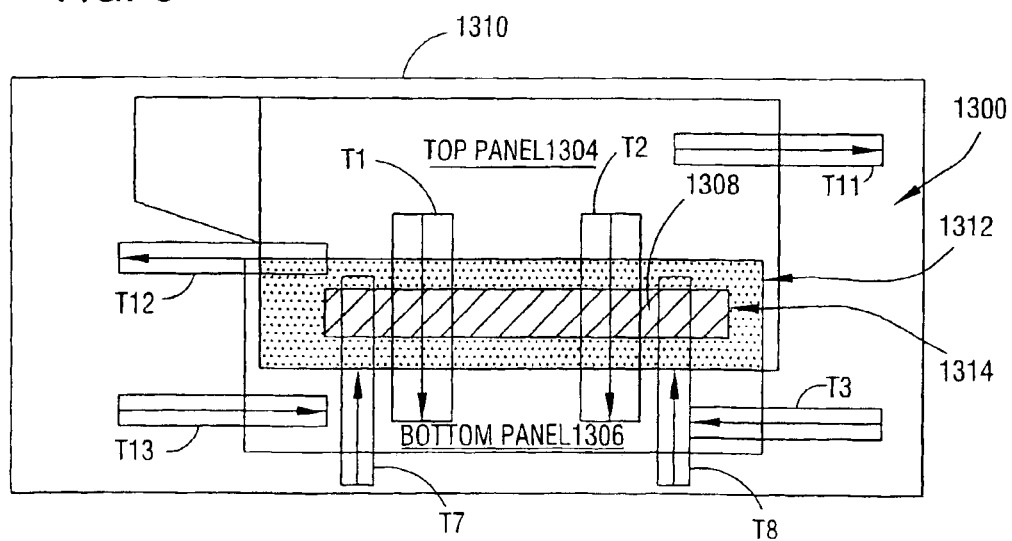
FIGS. 6 and 7 illustrate an image produced using the system of FIG. 5 of the inward view and the outward view, respectively, of an exemplary composite article including tool configurations therefor.
Figure 7:
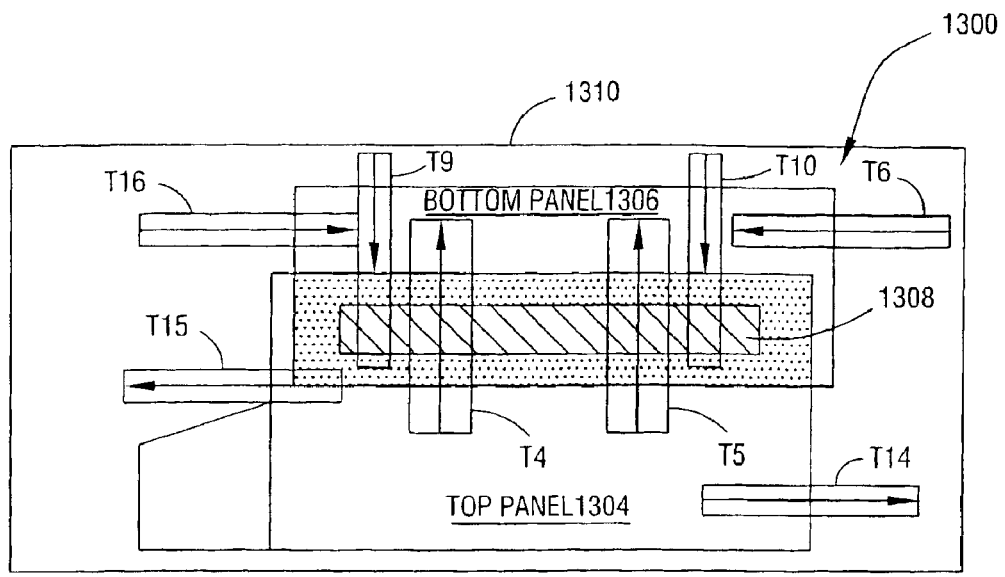

FIG. 6 illustrates an exemplary two dimensional black-and-white image 1310 of the inward side of the composite article 1300 as produced by the system 1200 of FIG. 5 employing an infrared source. FIG. 6 illustrates a top panel 1304 overlaying a bottom panel 1306 having a hook material 1308 therebetween. In particular, FIG. 6 is a view of an article looking inward at a web carrying the article. For example, FIG. 6 is the view of a camera positioned near an inward side of the web looking at the article on the web. FIG. 7 illustrates an corresponding outward view. FIG. 7 is the view of a camera positioned near an outward side of the web looking at the article on the web. (See FIG. 24 and camera 594 above). Inward and outward views may also be referred to as left and right views or near-side or far-side views. Although the views herein are referred to as inward and outward views within the context of a web, it is contemplated that the various aspects of the invention may be used with or without a web. In this example, shaded regions of the image 1310 correspond to portions of the composite article 1300 from which the camera 1206 received relatively less infrared radiation. Thus, a position of some contrast variation (e.g., from light to medium) at 1312 in the image 1310 represents a position of an edge of a bottom panel 1306. Similarly, a position of another contrast variation (e.g., from medium to dark) at 1314 in the image 1310 represents a position of an edge of the hook material 1308.

The underlying portion of the bottom panel 1306 appears shaded with dots in the image 1310 as compared to the unshaded portions of the top panel 1304, which do not overlie the bottom panel 1306. The shading indicates that the infrared radiation which passes through the bottom panel 1306 is partially absorbed or reflected by the top panel 1304. The hook material 1308 is cross-hatched to indicate even less radiation passing therethrough. In other words, upper components and lower components provide a cumulative absorptive and/or reflective effect in those regions where an upper component overlies a lower component. Therefore, the camera 1206 receives less infrared radiation transmitted through that portion of an upper component which overlies a lower component than it does through surrounding portions of the upper component (assuming all portions of the upper component uniformly inhibit the same amount of infrared radiation from passing therethrough, although this is not a requirement of the invention).

By processing the images of FIGS. 6 and 7, the image analyzer 1208 can identify positions of the aforementioned variations and thus provide identified presence and position data. In one embodiment, each pixel or element of the image is assigned a grayscale value of 0–255, where higher grayscale values represent areas from which relatively less infrared radiation was received by the camera 1206. The image analyzer identifies predefined variations in these grayscale values which correspond to the component positions. The analyzer 1208 then compares this position data with predefined position data to determine whether the upper component and the lower component are properly positioned in an absolute sense and/or with respect to one another, and output appropriate signals to the process controller.

With further reference to FIG. 5, the image analyzer 1208 may be, for example, a programmable digital computer, implemented in a variety of hardware and software configurations. Additionally, these various components of the system 1200 may be implemented singly or in combination without departing from the scope of the invention. For example, the controller with image analyzer 1208 may be implemented within a single programmable computer including software for comparing to the reference data 1214. It should also be understood that in any given embodiment of the invention, the combination of infrared radiation source (including its intensity and wavelength(s)), infrared detector, radiation source/detector geometry, detector filter (if any), and infrared markers (if any) can be selected as necessary to enhance detection of components of interest in a composite article.

From the above description, it should be apparent that the present invention can be used to determine, among other things, whether one or more components are present and properly positioned in a wide array of composite articles. In fact, to the extent that such components do not inherently provide an infrared response which readily permits their detection using incident infrared (or other) radiation and infrared detectors, such components can be provided with a suitable infrared marker so as to impart them with a desired response, as noted above.

While suited for a wide variety of applications, the present invention is particularly useful in the production of absorbent articles, such as disposable diapers, training pants, incontinence devices, sanitary napkins, and the like. Thus, one exemplary application of the invention for detecting component positions will now be described with reference to the disposable article 1500 (e.g., training pants) illustrated in FIG. 8, and with further reference to the exemplary detection system 1200 of FIG. 5. Exemplary systems and processes for producing the article 1500 are described in international application PCT/US01/15803, the disclosure of which is incorporated herein by reference.

Figure 8:
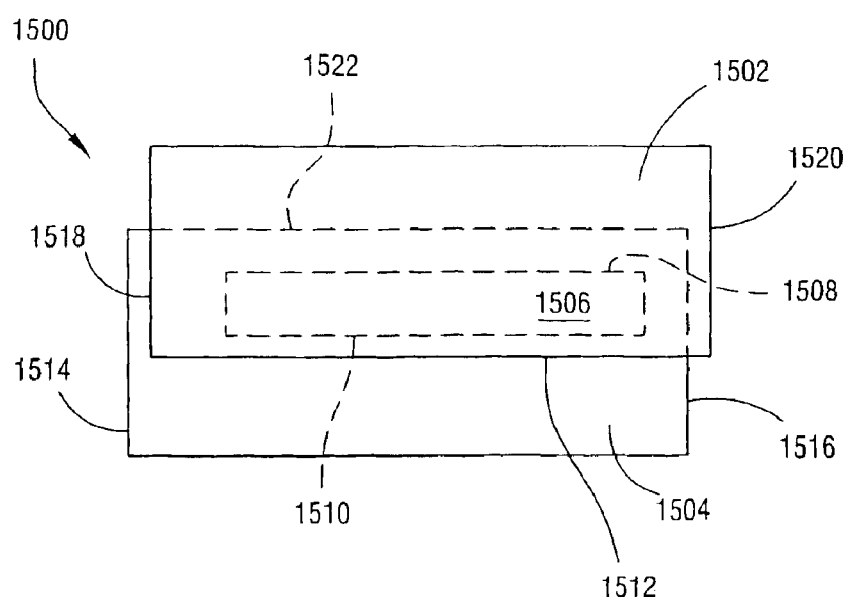
FIG. 8 is a top view of an exemplary disposable article having overlapping side panels.

In particular, FIG. 8 illustrates one end of a first side panel 1502 of the article 1500 joined with one end of a second side panel 1504 via a fastener component 1506 (shown in phantom) previously bonded to the second side panel 1504, and now disposed between the two side panels, with the first side panel 1502 overlapping the second side panel 1504 and the fastener component 1506. In this particular embodiment, the first side panel 1502 and the second side panel 1504 are each formed from a pigmented nonwoven material, such as a stretch bonded laminate (SBL), and the fastener component 1506 is one of a hook component and a loop component of a hook-and-loop fastener (e.g., a VELCRO brand fastener available from Velcro Industries B.V.). In this particular embodiment, a complementary fastener component (not shown) is also bonded to an underside of the first panel 1502, and mates with the fastener component 1506 bonded to the second side panel 1504. Alternatively, other types of fasteners, including similar-surface interlocking fasteners, may be used.

In some embodiments, incident radiation may be in the range of about 700–1200 nanometers. This is because many existing inspection systems (previously used only for detecting visible and/or ultraviolet radiation) can detect wavelengths of up to about 1200 nanometers, and can thus be readily configured for implemented aspects of the present invention. Further, the inventors have determined that infrared radiation having a wavelength of about 940 nanometers is especially well suited for penetrating and detecting positions of pigmented nonwoven materials, including stretch bonded laminates commonly employed in fabricating disposable diapers, training pants, and the like. Thus, the radiation source may emit radiation having a wavelength of about 940 nanometers (e.g., a commercially available infrared LED having a nominal value of 940 nanometers). Additionally, the camera 1206 used in the implementation described above with reference to FIG. 5 include a filter for removing (i.e., blocking) radiation, such as ambient and/or scattered radiation, having a wavelength of or below about 830 nanometers (e.g., a high pass filter having a nominal value of about 830 nanometers) including visible and ultraviolet radiation. Alternatively (or additionally), one or more shrouds may be employed around the camera 1206 to shield the detector from, e.g., extraneous radiation sources (such as ceiling lights, natural light, etc.).

With further reference to FIG. 5, it should be apparent that the system 1200 shown therein is capable of detecting presence and positions of not only stacked components, but also overlapping components as well as non-overlapping adjacent components. Further, the radiation source 1202 need not be an infrared radiation source in every application of the invention and, in fact, not be an infrared radiation source in certain embodiments, including one or more (but not all) embodiments where a component to be detected fluoresces in the infrared spectrum in response to incident radiation outside of the infrared spectrum. The radiation source may also emit multiple wavelengths or bands of wavelengths so as to cause multiple components which respond to different wavelengths of incident radiation (due to use of infrared markers or otherwise) to exhibit their responses simultaneously, thus permitting their simultaneous detection. In this regard, the camera 1206 may be only a single infrared sensor or array of sensors capable of detecting multiple wavelengths or wavelength ranges, and thus multiple components which exhibit different infrared responses to incident radiation. Alternatively, the camera 1206 may include multiple and distinct cameras, such as infrared cameras, and each of these detectors may be configured (via filters or otherwise) to detect distinct wavelengths or wavelength ranges. Of course, multiple systems of the types described herein may also be advantageously used in combination in any given application of the invention.

According to another aspect of the invention, the distribution of a plurality of components, each having a predefined response to incident radiation (due to use of infrared markers or otherwise), in a composite article may be readily determined. One exemplary process includes irradiating the composite article with the incident radiation, and producing an image from infrared radiation received from the composite article, where the image includes a pattern, formed by the predefined response of the composite articles, which corresponds to their distribution. This pattern is then compared to reference data (such as one or more predefined patterns corresponding to ideal or acceptable distributions) to determine whether the composite articles are properly distributed in the composite article. In one embodiment, the comparing includes performing a pattern matching function using a suitably configured computer device. This aspect of the invention is particularly useful in, for example, determining the distribution of absorbent particles, adhesives, and ointments used in fabrication of a disposable absorbent article.

Figure 9:
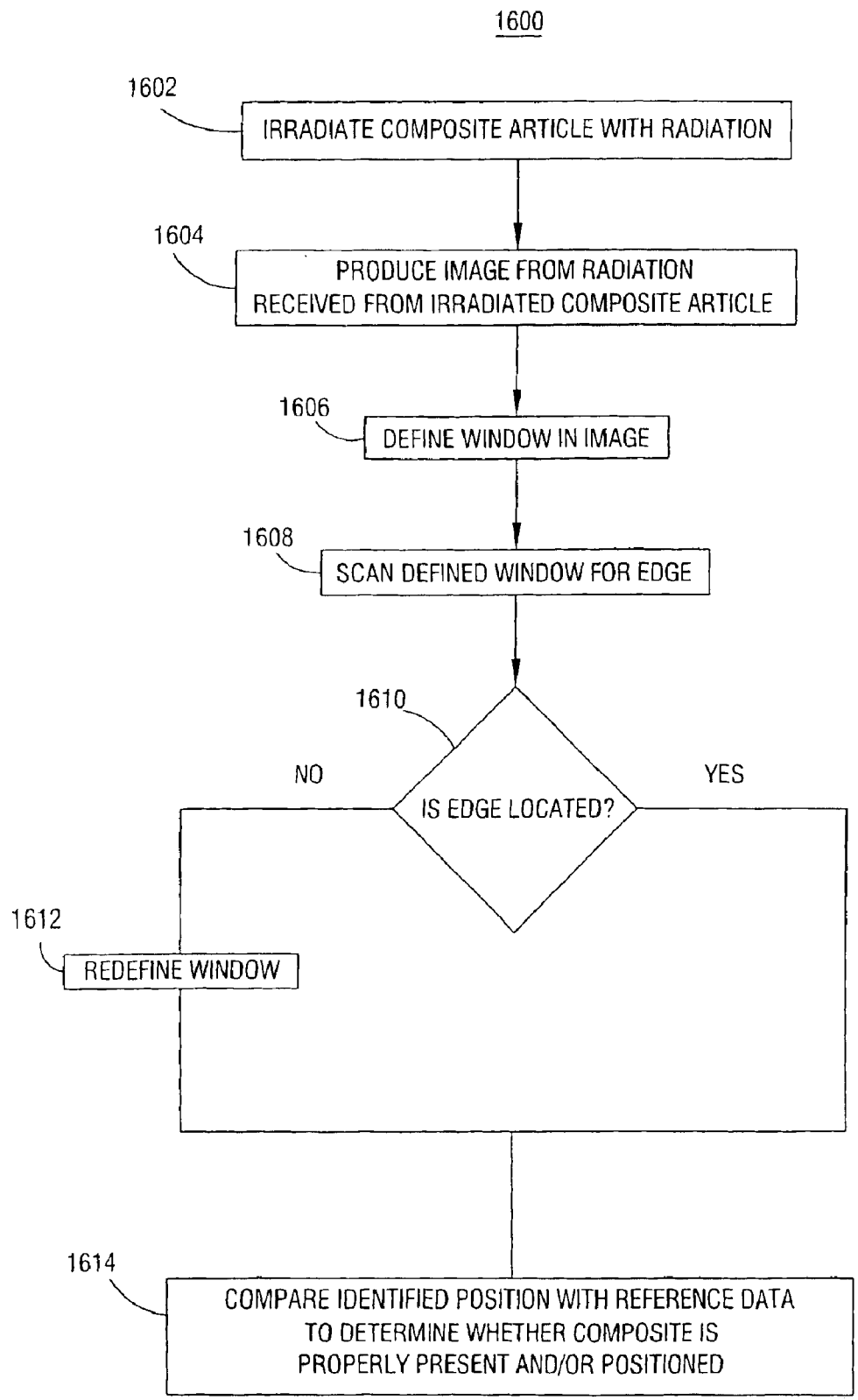
FIG. 9 is a flow diagram of a process for detecting whether one or more components are properly positioned in a composite article according to another preferred embodiment of the present invention including window redefinition.

FIG. 9 illustrates another embodiment of a process 1600 according to the invention of inspecting a composite article having first and second panels in at least partially opposed, overlapping engagement with each other and having an edge. The process 1600 determines whether the panels of the article are present and/or properly positioned. Initially, at 1602, the overlapping engagement of the panels is irradiated with radiation. Next, at 1604, an image is produced from the radiation received (either by transmission or reflection) from the irradiated panels. Next, at 1606, one or more windows in the image are defined. These windows designate areas which are evaluated by the imaging system. In particular, the imaging system scans for changes in intensity within the windows. As noted above, such changes in intensity indicate the location of an edge. Next, at 1608, the defined window(s) is scanned to identify any changes in intensity of the image and thereby determine a position of the edge. In the event that the edge is not located within the defined window during the scanning of the defined window, as determined at 1610, the window is redefined at 1612. This redefinition may include changing the scan direction (as noted below with respect to FIGS. 10–12), changing window position or size, changing scan parameters such as the amount or type of change in intensity to be detected, and/or any other window-related setting with regard to the window. Thereafter, at 1614, the determined presence and/or position of the component (e.g., an edge) is compared with a predetermined data to thereby determine whether the component is properly positioned in the composite article.

Two or more windows may be defined for each edge to be detected. Such windows are sometimes referred to as "tools". FIGS. 6 and 7 illustrate the windows or tools T of one preferred embodiment according to the invention. Each tool T is a rectangular area within which the image system scans for intensity differentials indicating a component such as an edge. The arrows in the rectangles indicate the direction of scan. In general, the image system looks at the pixels within the rectangle from one end to the other. The image system is programmed to look for a change in intensity in the pixels from lighter to darker or from darker to lighter, depending on whether the image system is searching for an underlying edge, an overlying edge or some other type of component.

The following Table 1 defines the tools T for the inward view illustrated in FIG. 6. The following Table 2 defines the tools T for the outward view illustrated in FIG. 7.

As shown in FIG. 6, tools T1 and T2 scan top to bottom to detect a horizontal edge of the hook material 1308. Tools T7 and T8 scan bottom to top to detect a horizontal edge of the top panel 1304. Tool T3 scans right to left to detect the trailing edge of bottom panel 1306. Tool T13 scans left to right to detect the leading edge of bottom panel 1306. Tool T11 scans left to right to detect a vertical edge of top panel 1304. Tool T12 scans right to left to detect a vertical edge of bottom panel 1306. As shown in FIG. 7, tools T4 and T5 scan bottom to top to detect a horizontal edge of the hook material 1308. Tools T9 and T10 scan top to bottom to detect a horizontal edge of the top panel 1304. Tool T6 scans right to left to detect the trailing edge of bottom panel 1306. Tool T16 scans left to right to detect the leading edge of bottom panel 1306. Tool T14 scans left to right to detect a vertical edge of top panel 1304. Tool T15 scans right to left to detect a vertical edge of bottom panel 1306. As used herein, top, bottom, left, right, leading, trailing, horizontal and vertical refer to and are with reference to the drawings and are exemplary terms.

TABLE 1

| Tool # | Inward View Tool Description |
| --- | --- |
| T1 | Hook Edge Pair Fixture @ Leg |
| T2 | Hook Edge Pair Fixture @ Waist |
| T3 | Trailing Edge |
| T7 | Loop/SBL Edge @ Leg |
| T8 | Loop/SEL Edge @ Waist |
| T11 | Waist Offset Edge |
| T12 | Leg Offset Edge |
| T13 | Leading Edge |

TABLE 2

| Tool # | Outward View Tool Description |
| --- | --- |
| T4 | Hook Edge Pair Fixture @ Leg |
| T5 | Hook Edge Pair Fixture @ Waist |
| T6 | Trailing Edge |
| T9 | Loop/SBL Edge @ Leg |

TABLE 2-continued

| Tool # | Outward View Tool Description |
|---|---|
| T10 | Loop/SBL Edge @ Waist |
| T14 | Waist Offset Edge |
| T15 | Leg Offset Edge |
| T16 | Leading Edge |

Figure 10:
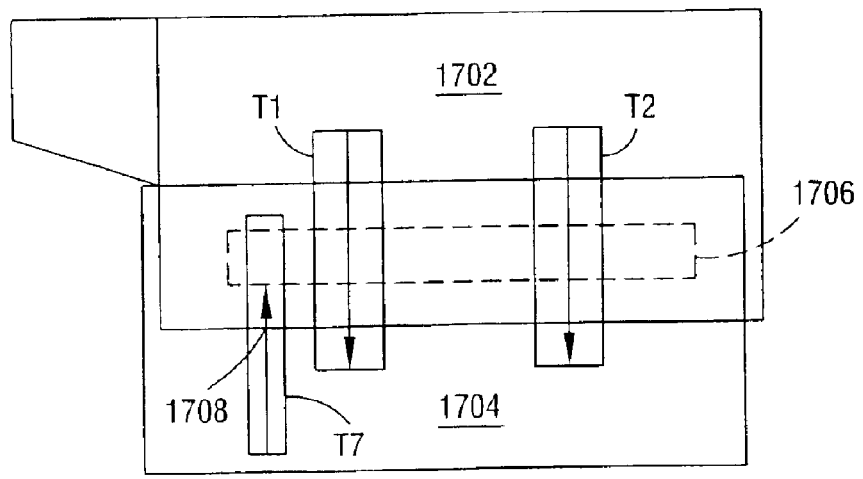
FIG. 10 illustrates an image produced using the system of FIG. 5 of the inward view of an exemplary composite article including tool configurations therefor wherein the components are properly positioned with respect to each other.
Figure 11:
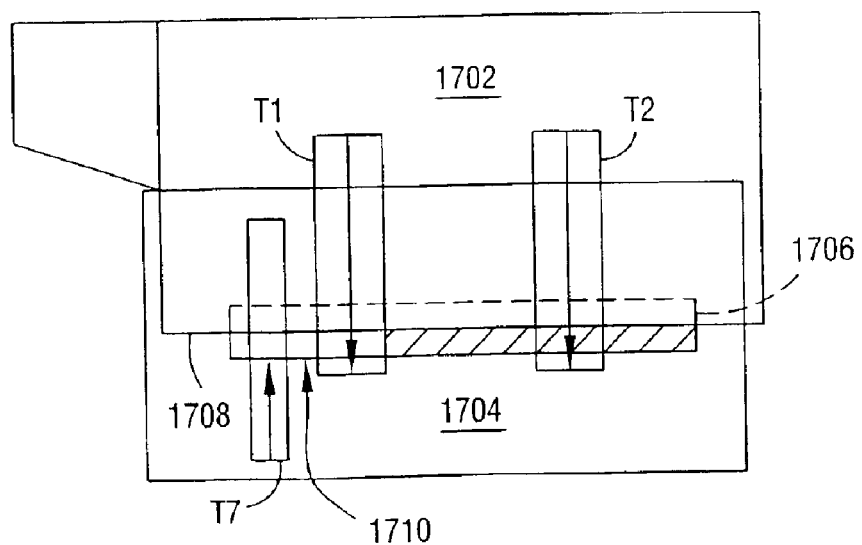
FIG. 11 illustrates an image produced using the system of FIG. 5 of the inward view of an exemplary composite article including tool configurations therefor wherein the components are positioned differently with respect to each other than FIG. 10 (e.g., an exposed hook material) resulting in an edge of the overlying panel being obscured.
Figure 12:
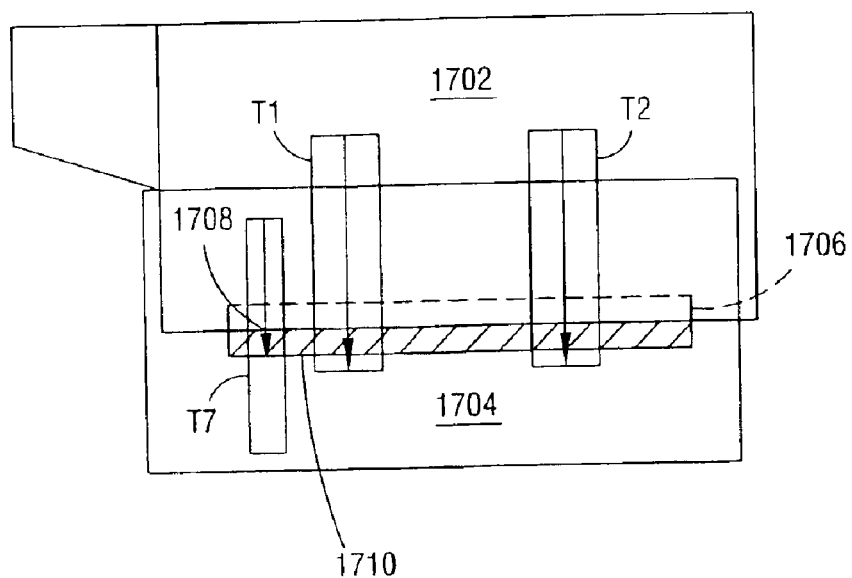
FIG. 12 illustrates an image produced using the system of FIG. 5 of the operator side of an exemplary composite article including tool configurations therefor wherein the components are positioned differently with respect to each other than FIG. 10 (e.g., an exposed hook material).

Referring also to FIGS. 10–12, which correspond to FIG. 6 with some tools removed, various configurations of the composite article are shown to illustrate one scenario in which a tool may be redefined. FIG. 10 illustrates the components in a substantially normal configuration wherein a top panel 1702 overlaps a bottom panel 1704 and a hook material 1706 is positioned therebetween. In this configuration, as noted above, tools T1 and T2 scan top to bottom to detect an edge of the hook material 1706. Tool T7 scans bottom to top looking for a light to dark transition to detect an edge 1708 of the top panel 1702 (referred to as the loop/SBL edge@ leg). In this normal configuration illustrated in FIG. 10, the top panel 1702 extends downward past the hook material 1706. Thus, as tool T7 scans upward from its bottom, it will detect a light to dark intensity change at edge 1708. Below edge 1708, the detected radiation is passing through the bottom panel 1704 only. Immediately above edge 1708, the detected radiation is passing through the bottom panel 1704 and the top panel 1702. Relatively less radiation will pass through the top and bottom panels above edge 1708 as compared to the radiation passing through the bottom panel only below edge 1708. Thus, this relative difference will be detected as a light to dark transition by tool T7.

FIG. 11 illustrates the components in a different configuration as compared to FIG. 10 wherein the top panel 1702 overlaps the bottom panel 1704 and the hook material 1706 is positioned therebetween and partially below the edge 1708. In this configuration, tools T1 and T2 scan top to bottom to detect an edge of the hook material 1706. Tool T7 scans bottom to top looking for a light to dark transition to detect edge 1708 of the top panel 1702. In this configuration, the hook material 1706 extends downward below the edge 1708. Thus, as tool T7 scans upward from its bottom, it will detect a light to very dark intensity change at edge 1710. Below edge 1710, the detected radiation is passing through the bottom panel 1704 only. Immediately above edge 1710, the detected radiation is passing through the bottom panel 1704 and the hook material 1706. Relatively much less radiation will pass through the hook material 1706 and the bottom panel 1704 above edge 1710 as compared to the radiation passing through the bottom panel only below edge 1710. Thus, this relative difference will be detected as a light to very dark transition by tool T7. However, tool T2 is looking for edge 1708 which is a light to dark, not a light to very dark, transition. As tool T7 continues to scan upward past edge 1710 to edge 1708, it encounters a very dark to extremely dark transition. Thus, tool T7 does not detect a light to dark transition and so that it is unable to locate edge 1708. In this event, tool T7 is programmed to be redefined to scan from top to bottom as shown in FIG. 12 looking for an extremely dark to very dark transition (approximately a 25% change).

FIG. 12 illustrates the components in a same configuration as FIG. 11 wherein the top panel 1702 overlaps the bottom panel 1704 and the hook material 1706 is positioned therebetween and partially below the edge 1708. In this configuration, tools T1 and T2 scan top to bottom to detect an edge of the hook material 1706. Tool T7 has been redefined to scan top to bottom looking for an extremely dark to very dark transition to detect edge 1708 of the bottom panel 1704. In this configuration (as in FIG. 11), the hook material 1706 extends downward below the edge 1708. Thus, as tool T7 scans downward from its top, it will detect an extremely dark to very dark intensity change at edge 1708. Immediately above edge 1708 as tool T7 scans downward, the detected radiation is passing through the bottom panel 1704, the hook material 1706 and the top panel 1702. Immediately below edge 1708, and between edge 1708 and edge 1710, the detected radiation is passing through the bottom panel 1704 and the hook material 1706. Relatively more radiation will pass through the hook material 1706 and the bottom panel 1704 below edge 1708 as compared to the radiation passing through the bottom panel 1704, hook material 1706 and top panel 1702 above edge 1708. Thus, this relative difference will be detected as an extremely dark to very dark transition by tool T7. Tool T7, which has been redefined to scan downward and look for edge 1708 which is an extremely dark to very dark transition, is now able to detect edge 1708.

It is also contemplated that a tool may be redefined in other ways if it is unable to find a particular transition. For example, the tool may be repositioned, changed in size or angle or otherwise modified.

As used herein, "infrared radiation source" refers to any device capable of emitting radiation in the infrared spectrum (i.e., radiation having a wavelength between about 700 nanometers and one millimeter), regardless of whether it also emits radiation in other spectrums. Some examples of infrared radiation sources suitable for certain embodiments of the present invention include infrared LEDs, mercury vapor lamps, argon lamps, arc lamps, lasers, etc. In contrast, "radiation source" refers to any device capable of emitting radiation in any spectrum, which may or may not include the infrared spectrum.

"Infrared detector" refers to any device having one or more sensor elements (including a matrix of sensor elements) capable of sensing infrared radiation, regardless of whether such device can also sense radiation in other spectrums. Thus, included in this definition are existing vision inspection cameras which are capable of detecting not only visible and ultraviolet light, but also infrared radiation of wavelengths up to about 1200 nanometers (as noted above), line scan cameras capable of building an image one line at a time from infrared radiation received from an article as the article is moved relative thereto, as well as any other device capable of producing a one, two or three dimensional image from received infrared radiation including, without limitation, a charge coupled device ("CCD").

As alluded to above, any infrared detector used in the present invention (as well as any composite article to be detected thereby) may be provided with a filter for filtering unwanted wavelengths, including those in the infrared and/or other spectrums, as desired. Such filters include low-pass filters which remove radiation above a predefined wavelength, high-pass filters which remove radiation below a predefined wavelength, band-pass filters which remove all radiation except that having a wavelength within a predefined range, and combinations thereof. One or more of these filters may be useful for removing ambient, scattered, or even incident radiation (such as when detecting components which fluoresce at different wavelengths than the incident radiation) in any given application of the invention.

The infrared and other radiation sources described herein, as well as the infrared detectors, may include fiber optic devices in various applications of the invention, such as to precisely irradiate or detect radiation from a specific component or region in a composite article.

Additionally, it should be understood that as used herein, the term "component" shall include not only discrete objects, but also objects yet to be formed into discrete objects (e.g., objects yet to be severed into discrete objects from a continuous sheet or web of material), particles (e.g., super-absorbent particles or polymers), adhesives, lotions, ointments, and other substances, as well as portions or characteristics of any such components including, for example, fold lines, bond lines (e.g., ultrasonic bond lines), bonded or adhered regions, edges and registration marks applied to or about components for subsequent detection during a manufacturing or inspection process. Indeed, the teachings of the invention can be used to detect the presence and/or position including physical, optical, and component structural properties for any composite article under observation.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed:

1. A process of inspecting a composite article having first and second panels in at least partially opposed, overlapping engagement with each other, the first panel having an underlying edge overlapped by at least a portion of the second panel which is substantially opaque to visible and/or ultraviolet light, said process to determine whether the panels of the article are present and/or properly positioned, said process comprising:

irradiating the overlapping engagement of the panels with radiation;

producing an image from radiation received from the irradiated panels;

identifying in the image a position of the underlying edge; and comparing the identified position of the underlying edge with a predetermined data to thereby determine whether the underlaying edge is present and/or properly positioned in the composite article.

2. The process of claim 1 wherein the irradiating includes irradiating the overlapping engagement of the panels with infrared radiation.

3. The process of claim 1 further comprising identifying in the image a position of an overlying edge of the composite article; and comparing the identified position of the overlying edge with predetermined data to thereby determine whether the first and second panels are properly positioned relative to each other in the composite article.

4. The process of claim 1 wherein the composite article comprises a disposable absorbent article.

5. The process of claim 4 wherein the disposable absorbent article includes a fastener at the overlapping engagement between the first and second panels.

6. A composite article processed using the process of claim 1.

7. The process of claim 1 further comprising defining a window and scanning the defined window for the underlying edge to determine its position.

8. The process of claim 7 further comprising redefining the defined window in the event that the underlying edge is not located within the defined window during scanning of the defined window.

9. A system for inspecting a composite article having first and second panels in at least partially opposed, overlapping engagement with each other, the first panel having an underlying edge overlapped by at least a portion of the second panel which is substantially opaque to visible and/or ultraviolet light, said system for determining whether the panels of the article are present and/or properly positioned, said system comprising:

a radiation source for irradiating the overlapping engagement of the panels with radiation;

a detector for producing an image from radiation received from the irradiated panels; and an image analyzer operatively connected to the detector for identifying in the image a presence and/or position of the underlying edge and for comparing the identified presence and/or position of the underlying edge with a predetermined data to thereby determine whether the underlying edge is present and/or properly positioned in the composite article.

10. The system of claim 9 wherein the source comprises an infrared radiation source.

11. The system of claim 9 wherein:

the image analyzer identifies in the image a position of an overlying edge of the composite article and compares the identified position of the overlying edge with a predetermined data to thereby determine whether the first and second panels are properly positioned relative to each other in the composite article.

12. The system of claim 9 wherein the composite article comprises a disposable absorbent article.

13. The system of claim 12 wherein the disposable absorbent article includes a fastener at the overlapping engagement between the first and second panels.

14. The system of claim 9 wherein the image analyzer defines a window and scans the defined window for the underlying edge to determine its position.

15. The system of claim 14 wherein the image analyzer redefines the defined window in the event that the underlying edge is not located within the defined window during scanning of the defined window.

16. A process of detecting one or more components in a composite article, the process comprising:
    irradiating the composite article with infrared radiation;
    producing an image from infrared radiation received from the irradiated composite article;
    identifying a position in the produced image corresponding to an underlying edge of a first component in the composite article, said underlying edge overlapped by at least a portion of a second component which is substantially opaque to visible and/or ultraviolet light; and
    comparing the identified position with predetermined position data to thereby determine whether the first component is present and/or properly positioned in the composite article.

17. The process of claim 16 wherein the producing includes providing an image of an underlying edge of the first component and wherein the identifying comprises identifying a position in the produced image corresponding to the underlying edge position of the first component in the composite article.

18. The process of claim 17 further comprising:
    identifying in the image a position of an overlying edge of the composite article; and
    comparing the identified position of the overlying edge with a predetermined data to thereby determine whether the first and second panels are properly positioned relative to each other in the composite article.

19. The process of claim 16 wherein the composite article comprises a disposable absorbent article.

20. The process of claim 19 wherein the disposable absorbent article includes a fastener at the overlapping engagement between the first and second panels.

21. A composite article, processed using the process of claim 16.

22. The process of claim 17 further comprising defining a window and scanning the defined window for the underlying edge to determine its position.

23. The process of claim 22 further comprising redefining the defined window in the event that the underlying edge is not located within the defined window during scanning of the defined window.

24. A system for detecting one or more components in a composite article, the process comprising:
    an infrared radiation source for irradiating the composite article with infrared radiation;
    an infrared detector for producing an image from infrared radiation received from the irradiated composite article; and
    an image analyzer operatively connected to the infrared detector for identifying a position in the produced image corresponding to an underlying edge of a first component in the composite article, said underlying edge overlapped by at least a portion of a second component which is substantially opaque to visible and/or ultraviolet light, said image analyzer further for comparing the identified position with predetermined position data to thereby determine whether the first component is present and/or properly positioned in the composite article.

25. The process of claim 24 wherein the infrared detector provides an image of an underlying edge of the first component and wherein the image analyzer identifies a position in the produced image corresponding to the underlying edge position of the first component in the composite article.

26. The process of claim 25 wherein: the image analyzer identifies in the image a position of an overlying edge of the composite article and compares the identified position of the overlying edge with a predetermined data to thereby determine whether the first and second panels are properly positioned relative to each other in the composite article.

27. The process of claim 24 wherein the composite article comprises a disposable absorbent article.

28. The process of claim 27 wherein the disposable absorbent article includes a fastener at the overlapping engagement between the first and second panels.

29. The process of claim 25 wherein the image analyzer defines a window and scans the defined window for the underlying edge to determine its position in the composite article.

30. The process of claim 29 wherein the image analyzer redefines the defined window in the event that the underlying edge is not located within the defined window during scanning of the defined window.

31. A process of inspecting a composite article having first and second panels in at least partially opposed, overlapping engagement with each ether and having an edge, said process to determine whether the panels of the article are properly positioned, said process comprising:
    irradiating the overlapping engagement of the panels with radiation;
    producing an image from radiation received from the irradiated panels;
    defining a window in the image;
    scanning the defined window to determine a position of the edge; redefining the window in the event that the edge is not located within the defined window during the scanning of the defined window; and
    comparing the determined position of the edge with a predetermined data to thereby determine whether the edge is properly positioned in the composite article.

32. The process of claim 31 wherein the irradiating including irradiating the overlapping engagement of the panels with infrared radiation.

33. The process of claim 31 further comprising:
    identifying in the image a position of an underlying edge of the composite article; and
    comparing the identified position of the underlying edge with a predetermined data to thereby determine whether the first and second panels are properly positioned relative to each other in the composite article.

34. The process of claim 33 further comprising:
    identifying in the image a position of an overlying edge of the composite article; and
    comparing the identified position of the overlying edge with a predetermined data to thereby determine whether the first and second panels are properly positioned relative to each other in the composite article.

35. The process of claim 31 wherein the composite article comprises a disposable absorbent article.

36. The process of claim 35 wherein the disposable absorbent article includes a fastener at the overlapping engagement between the first and second panels.

37. A composite article processed using the process of claim 31.

38. The process of claim 31 wherein the irradiating includes irradiating the overlapping engagement of the panels with infrared radiation.

39. A system for inspecting a composite article having first and second panels in at least partially opposed, overlapping engagement with each other and having an edge, said system for determining whether the panels of the article are properly positioned, said system comprising, a radiation source for irradiating the overlapping engagement of the panels with radiation;

a detector for producing an image from radiation received from the irradiated panels; and an image analyzer operatively connected to the detector for defining a window in the image, for scanning the defined window to determine a position of the edge, for redefining the window in the event that the edge is not located within the defined window during the scanning of the defined window, arid for comparing the determined position of the edge with a predetermined data to thereby determine whether the edge is properly positioned in the composite article.

40. The system of claim 39 wherein the source comprises an infrared radiation source.

41. The system of claim 39 wherein:

the image analyzer identifies in the image a position of an underlying edge of the composite article and compares the identified position of the underlying edge with a predetermined data to thereby determine whether the first and second panels are properly positioned relative to each other in the composite article.

42. The system of claim 41 wherein:

the image analyzer identifies in the image a position of an overlying edge of the composite article and compares the identified position of the overlying edge with a predetermined data to thereby determine whether the first arid second panels are properly positioned relative to each other.

43. The system of claim 39 wherein the composite article comprises a disposable absorbent article.

44. The system of claim 43 wherein the disposable absorbent article includes a fastener at the overlapping engagement between the first and second panels.

45. The system of claim 39 wherein the radiation source comprises an infrared radiation source.

* * * * *